US007025931B2

(12) United States Patent
Nuckols et al.

(10) Patent No.: US 7,025,931 B2
(45) Date of Patent: Apr. 11, 2006

(54) METHOD AND SYSTEM FOR REDUCING OXYGEN IN A CLOSED ENVIRONMENT

(75) Inventors: Marshall L. Nuckols, Annapolis, MD (US); Kirk Vanzandt, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 756 days.

(21) Appl. No.: 10/034,039

(22) Filed: Dec. 31, 2001

(65) Prior Publication Data

US 2003/0124032 A1 Jul. 3, 2003

(51) Int. Cl.
*A61L 9/00* (2006.01)
*A62B 7/08* (2006.01)

(52) U.S. Cl. ............................ 422/3; 96/146; 126/208; 422/4; 422/120; 422/122; 423/351

(58) Field of Classification Search .................... 422/3, 422/4, 120, 122; 423/351; 126/208; 96/146
See application file for complete search history.

(56) References Cited

U.S. PATENT DOCUMENTS

| | | | | |
|---|---|---|---|---|
| 4,304,752 | A * | 12/1981 | Jenkins et al. | 422/98 |
| 5,318,759 | A * | 6/1994 | Campbell et al. | 423/351 |
| 6,463,925 | B1 * | 10/2002 | Nuckols et al. | 126/208 |
| 6,508,866 | B1 * | 1/2003 | Golben | 96/146 |
| 6,528,403 | B1 * | 3/2003 | Tanabe et al. | 438/592 |
| 6,551,474 | B1 * | 4/2003 | Andrews et al. | 204/266 |

* cited by examiner

*Primary Examiner*—Krisanne Jastrzab
(74) *Attorney, Agent, or Firm*—James T. Shepherd

(57) ABSTRACT

The present invention reduces the amount of oxygen in an oxygen-containing gas within a closed environment. A selected amount of hydrogen gas is mixed with a portion of the oxygen-containing gas from the closed environment to form a first gas mixture. A catalyst exposed to the first gas mixture causes a reaction between the hydrogen and at least a portion of the oxygen therein. The resulting second gas mixture, which is returned to the closed environment, has a lower percentage of oxygen. At least one oxygen sensor is positioned in the closed environment to determine when oxygen levels in the closed environment reach a threshold level. The output signal from the sensor is used to control when and/or how much hydrogen is mixed in the first gas mixture.

19 Claims, 2 Drawing Sheets

METHOD AND SYSTEM FOR REDUCING OXYGEN IN A CLOSED ENVIRONMENT

ORIGIN OF THE INVENTION

The invention described herein was made in the performance of official duties by employees of the Department of the Navy and may be manufactured, used, licensed by or for the Government for any governmental purpose without payment of any royalties thereon.

CROSS-REFERENCE TO RELATED PATENT APPLICATIONS

This patent application is co-pending with one related patent application entitled "METHOD AND SYSTEM FOR HEATING AND HUMIDIFYING A BREATHABLE GAS", Ser. No. 09/448,405, filed Nov. 22, 1999, and owned by the same assignee as this patent application.

FIELD OF THE INVENTION

The invention relates generally to the reduction or removal of a gas from a closed environment, and more particularly to a method and system for reducing oxygen levels in closed environments where oxygen toxicity or flammability is a concern.

BACKGROUND OF THE INVENTION

The U.S. Navy is committed to maintaining and improving its systems and techniques used to rescue survivors from a disabled submarine. Rescue operations can be required in a variety of situations to include those where the disabled submarine becomes internally pressurized due to flooding, leakage of compressed gas supplies, or through use of auxiliary breathing systems.

Efficient submarine rescue requires that pressurized crew members be decompressed more rapidly than current decompression procedures allow when using air. It has been shown that crew decompression can be accelerated significantly by having crew members pre-breath oxygen using, for example, face masks supplied with either pure oxygen or an oxygen-rich breathing gas. Unfortunately, such oxygen pre-breathing can result in oxygen buildup in the cabin atmospheres of the submarine through leakage around the face seal of the oxygen masks or leakage from the oxygen supply. High levels of oxygen can create hazardous conditions within the cabin atmosphere due to increased fire potential and/or oxygen toxicity.

SUMMARY OF THE INVENTION

Accordingly, it is an object of the present invention to provide a method and system for reducing unsafe levels of oxygen in a closed environment.

Another object of the present invention to provide a method and system for monitoring and maintaining safe oxygen levels in a closed environment.

Still another object of the present invention to provide a method and system for monitoring and maintaining safe oxygen levels in a closed environment that is submerged in high ambient pressures.

Other objects and advantages of the present invention will become more obvious hereinafter in the specification and drawings.

In accordance with the present invention, a method and system are provided for reducing the amount of oxygen in an oxygen-containing gas within a closed environment. A controllable mixer, in response to a control signal, mixes a selected amount of hydrogen gas with a portion of the oxygen-containing gas from the closed environment to form a first gas mixture that includes hydrogen and oxygen. A catalyst coupled to the mixer receives the first gas mixture and causes a reaction between the hydrogen therein and at least a portion of the oxygen therein. As a result, a second gas mixture is formed. The second gas, which is then returned to the closed environment, has a lower percentage of oxygen than the first gas mixture. At least one oxygen sensor, positioned in the closed environment, is coupled to the mixer to generate the mixer's control signal when oxygen levels in the closed environment reach a threshold level.

DETAILED DESCRIPTION OF THE INVENTION

Figure 1:
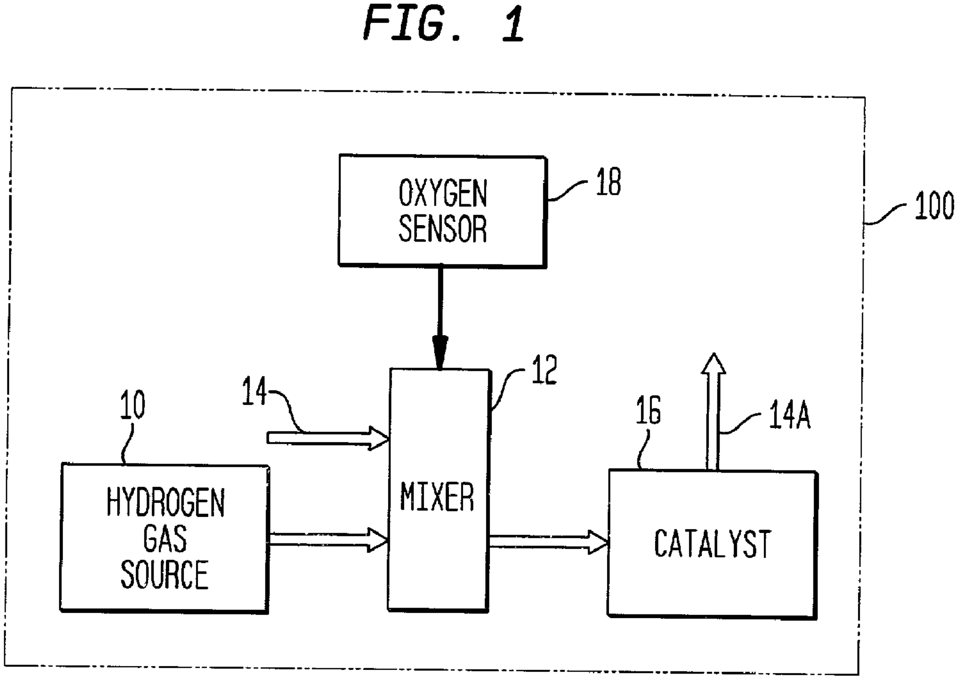
FIG. 1 is a top-level block diagram of a system used to monitor and reduce oxygen levels in a closed environment in accordance with the present invention.

Referring now to the drawings, and more particularly to FIG. 1, a system for reducing oxygen levels in a closed environment is illustrated in functional block diagram form. More specifically, the closed environment is designated by box 100 and is representative of any closed cabin maintained in space, on the earth's surface or underwater. As will become apparent from the following description, the present invention is particularly useful for closed environments that cannot be vented directly to the surrounding environment. Accordingly, by way of illustrative example, the features of the present invention will be described generally with respect to closed environments that are submerged in water.

In general, the present invention includes: a source 10 of hydrogen gas; a mixer 12 coupled to source 10 and configured to receive therein (as referenced by arrow 14) an oxygen-containing gas maintained within closed environment 100 and a controlled amount of hydrogen gas from source 10; a reaction-facilitating catalyst 16 coupled to mixing chamber 12 for facilitating a reaction between hydrogen and oxygen present in mixer 12 to effectively reduce the oxygen level therein and return the reduced-oxygen gas 14A to closed environment 100; and an oxygen sensor 18 coupled to mixer 12 to monitor oxygen levels in closed environment 100 and provide a control signal indicative thereof to mixer 12.

Source 10 can be any suitable source of hydrogen such as a tank of pure pressurized or unpressurized hydrogen gas or a metal hydride material that can be treated to release hydrogen gas as is well known in the art. Source 10 can be maintained within (as shown) or outside of closed environment 100 depending on the particular application needs. For example, if closed environment 100 is an underwater cabin and source 10 is a container of pressurized hydrogen gas, it is preferred to keep source 10 out of closed environment 100 for safety reasons.

Figure 2:
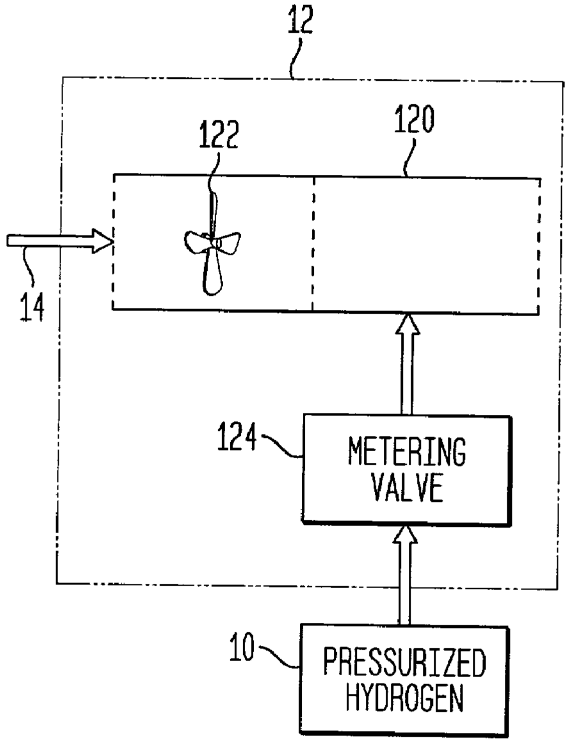
FIG. 2 is a schematic view of an embodiment of the mixer used in the present invention.

Mixer 12 is representative of any controllable device/system that mixes hydrogen gas from source 10 with oxygen-containing gas 14 from closed environment 100 whenever oxygen sensor 18 indicates that oxygen levels in closed environments 100 have achieved a threshold level, i.e., oxygen levels need to be reduced. Mixer 12 can be achieved in a variety of ways without departing from the scope of the present invention. For example, as illustrated in FIG. 2, mixer 12 could be realized by an open or flow-through chamber 120 having a fan 122 disposed at one end thereof for sucking in oxygen-containing gas 14 from closed environment 100. A metering valve 124 is disposed between a (pressurized) hydrogen source 10 and chamber 120 to control the flow of hydrogen into chamber 120. The opening/closing of metering valve 124 is controlled by a control signal received from oxygen sensor 18.

Figure 3:
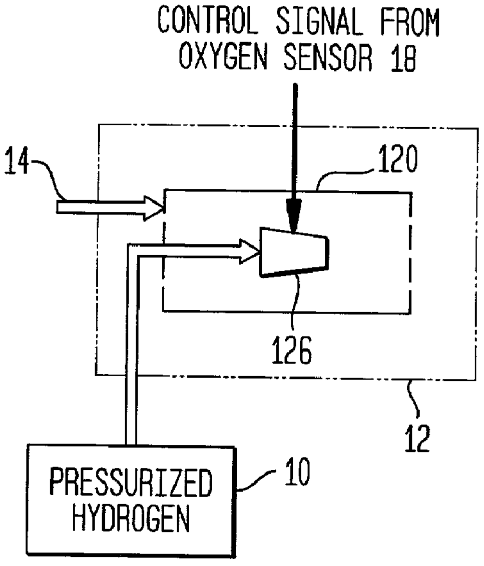
FIG. 3 is a schematic view of another embodiment of the mixer used in the present invention.

Another embodiment of mixer 12 is illustrated in FIG. 3 where flow-through chamber 120 has a controllable jet nozzle 126 disposed therein. A (pressurized) hydrogen source 10 is coupled to jet nozzle 126. The opening/closing of jet nozzle 126 is controlled by a control signal received from oxygen sensor 18. When jet nozzle 126 is opened so that pressurized hydrogen gas is injected into chamber 120, oxygen-containing gas 14 is drawn into chamber 120 and mixed with the injected hydrogen gas. It is to be understood that other embodiments of mixer 12 can be used, and that those disclosed herein are not limitations of the present invention.

When oxygen sensor 18 detects a pre-determined threshold oxygen level in closed environment 100, mixer 12 generates a gas mixture that consists of oxygen-containing gas 14 and hydrogen gas from source 10. This gas mixture is provided or exposed to catalyst 16 that will facilitate a reaction between the hydrogen and oxygen constituents in the gas mixture. Specifically, catalyst 16 is selected to facilitate the reaction of each one mole of hydrogen with one-half mole of oxygen ($1H_2+\frac{1}{2}O_2$). This reaction produces water vapor ($H_2O$) and heat (103,968 Btu/mol $H_2$) within the gas mixture. Catalyst 16 can be any material that facilitates the above-described reaction. In tests, precious metal (e.g., palladium, platinum, etc.) catalysts have performed well. While the catalyst could make use of these precious metals in their pure form, cost considerations will generally dictate that the catalyst material be supported or suspended on some lesser expensive material such as carbon, alumina, ceramics, etc. For example, the catalyst material could be surface-deposited on granular or particle-sized particles of a support matrix such as 0.8% (weight percentage) palladium deposited on extruded pellets of carbon which is available commercially from Engelhard Corporation, Seneca, S.C.

From a safety perspective, the volume percentage of hydrogen must remain well below the level at which oxygen and hydrogen would combust as is well known in the art. To achieve such safety levels, the volume percentage of hydrogen gas mixed with oxygen-containing gas 14 is generally on the order of approximately 1% or less.

oxygen sensor 18 is representative of any suitable sensor and/or sensor system that can detect the desired threshold level of oxygen and generate a control signal for mixer 12 as described above. Although only one oxygen sensor 18 is shown, there will typically be multiple oxygen sensors distributed throughout closed environment 100. Thus, the particular type and number of oxygen sensors are not limitations of the present invention.

Figure 4:
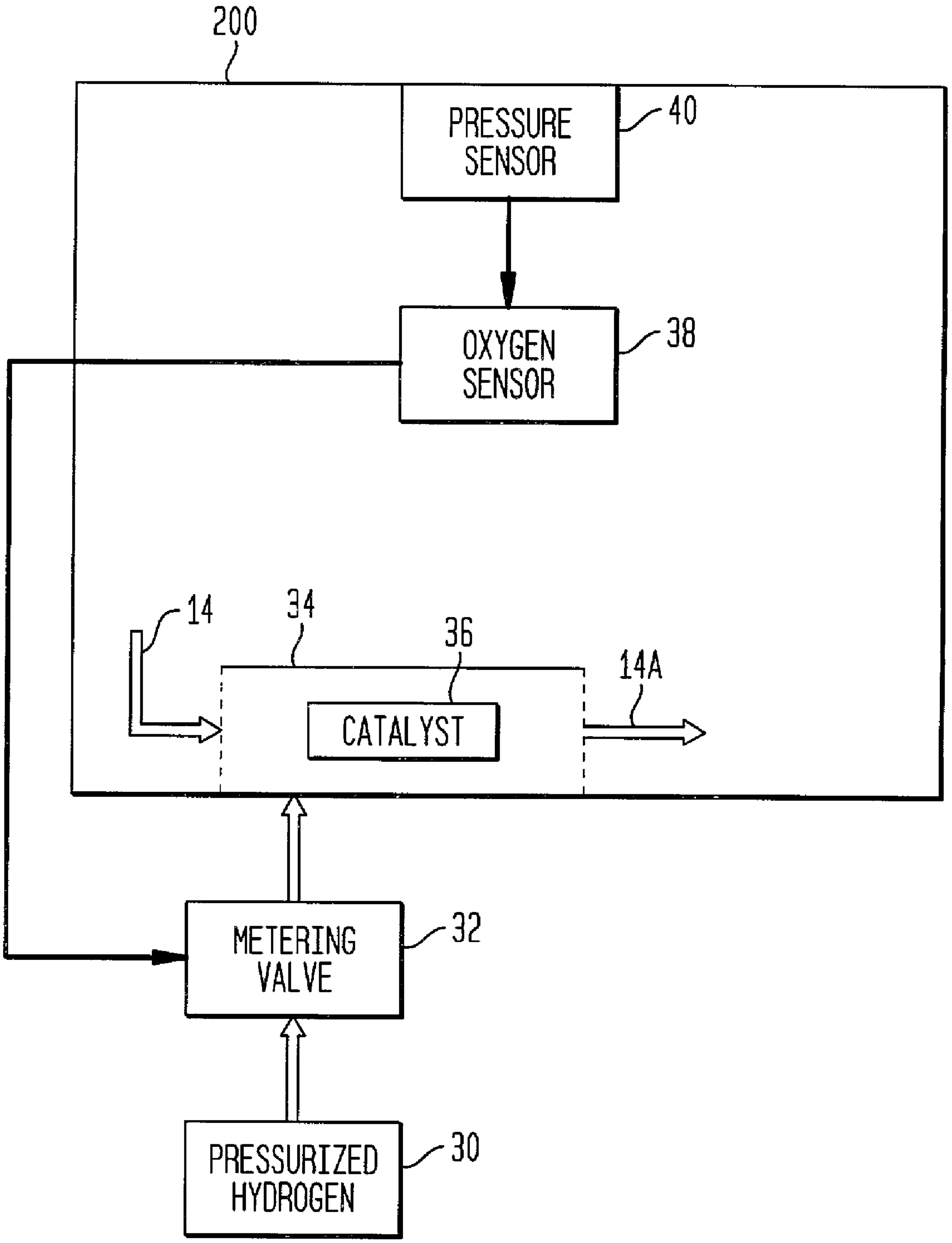
FIG. 4 is a schematic view of an embodiment of a system used to monitor and reduce oxygen levels in a sealed underwater cabin in accordance with the present invention.

By way of illustrative example, an embodiment of the present invention useful for monitoring and reducing oxygen levels in a sealed and submerged underwater cabin 200 is illustrated in FIG. 4. A pressurized source 30 of hydrogen gas is maintained outside of closed environment 200 for safety reasons. A metering valve 32 couples source 30 to a flow-through chamber 34 maintained in closed environment 200. Metering valve 32 can be maintained outside of or inside closed environment 200. Chamber 34 could be part of the ventilation system (e.g., duct work) used in closed environment 200. Disposed in chamber 34 is a catalyst 36 analogous to catalyst 16 described above. An oxygen sensor 38 disposed in closed environment 200 has its control signal output coupled to metering valve 32. The operation of sensor 38 and metering valve 32 is analogous to that described above with respect to sensor 18 and metering valve 124. A pressure sensor 40, disposed to measure ambient pressure inside closed environment 200, is coupled to oxygen sensor 38 for reasons that will be explained further below.

In operation of the system illustrated in FIG. 4, when oxygen sensor 38 detects an unacceptable level of oxygen in closed environment 200, metering valve 32 is opened and oxygen-containing gas 14 flowing through chamber 34 is mixed with injected hydrogen gas. This gas mixture is exposed to catalyst 36 where the ensuing hydrogen/oxygen reaction reduces the oxygen in the gas 14A returned to closed environment 200.

Since closed environment 200 is assumed to be underwater, ambient cabin pressure within closed environment 200 factors into what level of oxygen is unacceptable. For example, at surface pressure (1 atmosphere), acceptable oxygen levels comprise a 16–50% oxygen content in the breathing gas. However, note that in determining acceptable levels of oxygen, one must also take into consideration that fire hazards in the cabin increase directly with oxygen percentage in the atmosphere. Typically, a maximum of 25% oxygen is recommended in the cabin atmosphere to minimize fire hazards.

In contrast to surface pressure conditions, elevated atmospheric pressures that may exist in a flooded submarine cause the acceptable oxygen percentages to be reduced inversely to pressure. That is, if the cabin atmosphere is twice that of normal atmospheric pressure, then the acceptable oxygen content will be halved to 8–25% oxygen; if the cabin pressure is five times normal pressure, then the oxygen content will be one fifth; etc. Accordingly, measurements of ambient cabin pressure by pressure sensor 40 can be used to change the threshold level of oxygen sensor 38 so that the present invention adapts to changing ambient cabin pressure conditions.

The advantages of the present invention are numerous. Oxygen levels in a closed environment are monitored and maintained to provide a safe breathable atmosphere for the closed environment's occupants. The system and method are simple and can be adapted to any closed environment used in space, on the ground or underwater.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

The invention claimed is:

1. A system for reducing the amount of oxygen in an oxygen-containing gas within a closed environment, comprising:

a source of hydrogen gas;

a controllable means for mixing, in response to a control signal, a selected amount of said hydrogen gas with a portion of said oxygen-containing gas from said closed environment to form a first gas mixture that includes hydrogen and oxygen;

a catalyst coupled to said controllable means for receiving said first gas mixture, said catalyst causing a reaction between said hydrogen and at least a portion of said oxygen in said first gas mixture wherein a second gas mixture is formed and returned to said closed environment, said second gas mixture (i) having a lower percentage of oxygen than said first gas mixture, and (ii) containing oxygen in an amount sufficient to make said second gas mixture breathable; and at least one oxygen sensor positioned in said closed environment and coupled to said controllable means for generating said control signal when oxygen levels of said oxygen-containing gas in said closed environment reach a threshold level defined for an ambient pressure in said closed environment.

2. A system as in claim 1 wherein said source contains said hydrogen gas in its pure form.

3. A system as in claim 1 wherein said source of said hydrogen gas comprises a metal hydride material.

4. A system as in claim 1 wherein a volume percentage of said hydrogen gas in said first gas mixture is less than approximately one percent.

5. A system as in claim 1 wherein said catalyst is a precious metal.

6. A system as in claim 5 wherein said precious metal is selected from the group consisting of palladium and platinum.

7. A system as in claim 1 wherein said reaction caused by said catalyst is defined by a reaction of one-half mole of said oxygen in said first gas mixture with one mole of said hydrogen in said first gas mixture to produce water vapor and heat.

8. A system for reducing the amount of oxygen in an oxygen-containing gas within a closed environment, comprising:

a source of hydrogen gas under pressure;

a controllable valve having an input and an output, said input coupled to said source, said controllable valve dispensing a variable amount of said hydrogen gas from said input to said output in accordance with a control signal;

a chamber coupled to said output of said controllable valve for receiving therein said variable amount of said hydrogen gas so-dispensed;

means coupled to said chamber for drawing a portion of said oxygen-containing gas from said closed environment into said chamber wherein said variable amount of said hydrogen gas and said portion of said oxygen-containing gas combine to form a first gas mixture that includes hydrogen and oxygen;

a catalyst coupled to said chamber for receiving said first gas mixture, said catalyst causing a water vaporproducing reaction between said hydrogen and at least a portion of said oxygen in said first gas mixture wherein a second gas mixture is formed and returned to said closed environment, said second gas mixture (i) having a lower percentage of oxygen than said first gas mixture, and (ii) containing oxygen in an amount sufficient to make said second gas mixture breathable; and at least one oxygen sensor positioned in said closed environment and coupled to said controllable valve for generating said control signal when oxygen levels of said oxygen-containing gas in said closed environment reach a threshold level defined for an ambient pressure in said closed environment.

9. A system as in claim 8 wherein a volume percentage of said hydrogen gas in said first gas mixture is less than approximately one percent.

10. A system as in claim 8 wherein said catalyst is a precious metal.

11. A system as in claim 10 wherein said precious metal is selected from the group consisting of palladium and platinum.

12. A system as in claim 8 wherein said source of said hydrogen gas under pressure is maintained outside of said closed environment.

13. A system as in claim 8 wherein said reaction caused by said catalyst is defined by a reaction of one-half mole of said oxygen in said first gas mixture with one mole of said hydrogen in said first gas mixture.

14. A system as in claim 8 further comprising a pressure sensor for measuring said ambient pressure inside said closed environment, said pressure sensor coupled to said at least one oxygen sensor wherein said threshold level is adjusted in accordance with said ambient pressure so-measured.

15. A method of reducing the amount of oxygen in an oxygen-containing gas within a closed environment, comprising the steps of:

monitoring oxygen levels in said closed environment;

generating a control signal when said oxygen levels in said closed environment reach a threshold level defined for an ambient pressure in said closed environment;

mixing, in response to a control signal, a selected amount of hydrogen gas with a portion of said oxygen-containing gas from said closed environment to form a first gas mixture that includes hydrogen and oxygen;

exposing said first gas mixture to a catalyst capable of causing a reaction between said hydrogen and at least a portion of said oxygen in said first gas mixture wherein a second gas mixture is formed, said second gas mixture (i) having a lower percentage of oxygen than said first gas mixture, and (ii) containing oxygen in an amount sufficient to make said second gas mixture breathable; and dispensing said second gas mixture into said closed environment.

16. A method according to claim 15 wherein said reaction produces water vapor.

17. A method according to claim 15 wherein a volume percentage of said hydrogen gas in said first gas mixture is less than approximately one percent.

18. A method according to claim 15 wherein said step of mixing comprises the steps of:

providing an open chamber in said closed environment; and injecting said hydrogen gas into said open chamber under pressure to draw said oxygen-containing gas into said open chamber.

19. A method according to claim 15 further comprising the steps of:

measuring said ambient pressure inside said closed environment; and adjusting said threshold level in accordance with said ambient pressure so-measured.

* * * * *